United States Patent
Dubovoy et al.

(10) Patent No.: US 12,012,338 B2
(45) Date of Patent: Jun. 18, 2024

(54) ZIRCONIUM-BASED CLUSTER AS A DENTIN TUBULE OCCLUSION AGENT

(71) Applicant: Colgate-Palmolive Company, New York, NY (US)

(72) Inventors: Viktor Dubovoy, Cresskill, NJ (US); Irene Petrou, Parsippany, NJ (US); Long Pan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 456 days.

(21) Appl. No.: 16/216,262

(22) Filed: Dec. 11, 2018

(65) Prior Publication Data

US 2019/0185339 A1 Jun. 20, 2019

Related U.S. Application Data

(60) Provisional application No. 62/598,508, filed on Dec. 14, 2017.

(51) Int. Cl.
| | |
|---|---|
| *C01G 25/04* | (2006.01) |
| *A61K 8/21* | (2006.01) |
| *A61K 8/28* | (2006.01) |
| *A61K 8/44* | (2006.01) |
| *A61Q 11/00* | (2006.01) |
| *C01F 5/10* | (2006.01) |

(Continued)

(52) U.S. Cl.
CPC .............. *C01G 25/04* (2013.01); *A61K 8/21* (2013.01); *A61K 8/28* (2013.01); *A61K 8/44* (2013.01); *A61Q 11/00* (2013.01); *C01F 5/10* (2013.01); *C01G 25/00* (2013.01); *A61K 2800/413* (2013.01); *A61K 2800/805* (2013.01); *B82Y 30/00* (2013.01); *B82Y 40/00* (2013.01); *C01P 2002/87* (2013.01); *C01P 2004/64* (2013.01)

(58) Field of Classification Search
CPC ... A61K 8/28; A61K 8/22; A61K 8/21; A61K 8/44; A61K 2800/413; A61K 2800/805; C01G 25/04; C01G 25/00; A61Q 11/00; B82Y 30/00; B82Y 40/00; C01F 5/10; C01P 2002/87; C01P 2004/64
See application file for complete search history.

(56) References Cited

U.S. PATENT DOCUMENTS

| | | | | |
|---|---|---|---|---|
| 3,981,986 A | * | 9/1976 | Rubino | .............. A61K 8/28 424/47 |
| 4,148,812 A | * | 4/1979 | Rubino | .............. A61K 8/042 556/55 |

(Continued)

FOREIGN PATENT DOCUMENTS

| | | |
|---|---|---|
| CN | 103705390 | 4/2014 |
| WO | 2013/158077 | 10/2013 |
| WO | 2016/048340 | 3/2016 |

OTHER PUBLICATIONS

Coordination compound: retrieved from internet: https://academic.eb.com/levels/collegiate/article/coordination-compound/26165#277784.toc. Retrieved on Oct. 19, 2021.*

(Continued)

*Primary Examiner* — Hong Yu

(57) ABSTRACT

Described herein are zirconium oxychloride clusters comprising zirconium oxychloride and a basic amino acid. Oral care compositions comprising the same; and methods of making and using the same are also described.

7 Claims, 3 Drawing Sheets

(51) Int. Cl.
  *C01G 25/00*     (2006.01)
  *B82Y 30/00*     (2011.01)
  *B82Y 40/00*     (2011.01)

(56)           References Cited

U.S. PATENT DOCUMENTS

| | | | |
|---|---|---|---|
| 4,859,446 A * | 8/1989 | Abrutyn | A61K 8/26 |
| | | | 423/462 |
| 5,718,876 A | 2/1998 | Parekh et al. | |
| 5,792,446 A * | 8/1998 | Ashley | A61K 8/11 |
| | | | 424/52 |
| 8,257,689 B2 | 9/2012 | Pan | |
| 8,562,956 B2 | 10/2013 | Pan | |
| 8,603,505 B2 | 12/2013 | Brown et al. | |
| 8,795,641 B2 | 8/2014 | Pan | |
| 9,427,386 B2 | 8/2016 | Pan | |
| 10,206,858 B2 | 2/2019 | Dubovoy et al. | |
| 2010/0202993 A1 | 8/2010 | Pan | |
| 2015/0132242 A1 | 5/2015 | Yuan | |

OTHER PUBLICATIONS

Radius of gyration: retrieved from internet: https://goldbook.iupac.org/terms/view/R05121. Retrieved on Oct. 19, 2021.*
Radius of gyration: retrieved from internet: https://physicscatalyst.com/mech/radius-of-gyration.php. Retrieved on Oct. 19, 2021.*
International Search Report and Written Opinion of the International Searching Authority in International Application PCT/US2018/064908, dated May 22, 2019.

* cited by examiner

ZIRCONIUM-BASED CLUSTER AS A DENTIN TUBULE OCCLUSION AGENT

CROSS REFERENCE TO RELATED APPLICATIONS

This application claims the benefit and priority of U.S. provisional application 62/598,508, filed on Dec. 14, 2017.

BACKGROUND

Dentin hypersensitivity is a painful response to a variety of stimuli, including thermal, tactile, evaporative, osmotic, and chemical stimuli. Dentin is a portion of the tooth internal to the enamel and cementum that has a radially striated appearance owing to a large number of fine canals or tubules known as dentin tubules. Dentin tubules run from the pulp cavity to the periphery of the dentin and are generally about two microns in diameter at their base and somewhat narrower at their periphery. Dentin tubules are not usually exposed to the environment in the oral cavity, as they are usually covered by enamel or cementum. The cementum in turn is often covered by the gums. Partially or fully exposed tubules can lead to tooth sensitivity.

Conventionally, two approaches have been taken to treat or ameliorate tooth sensitivity. The first approach is to interfere with transmission of nerve impulses. Known desensitizing agents useful in this chemical approach include potassium salts (such as potassium nitrate, potassium bicarbonate, potassium chloride) and strontium, zinc salts, and chloride salts. The second approach involves the mechanical shield of the nerve by, e.g., blocking of the dentin tubules wholly or partially with dentin tubule occlusion agents. For example, arginine-calcium carbonate complexes plug dentinal tubules, providing immediate relief from dentinal hypersensitivity.

Zirconium salts have been used in antiperspirant formulations. Such zirconium compounds include acidic zirconium salts such as zirconium oxychloride or zirconyl chloride, zirconium hydroxychloride, and other halide and sulfate substitutes of the salts. Due to the large charge to size ratio of $Zr^{4+}$, zirconium compounds provide superior sweat reduction efficacy but has a high skin irritation potential. According to FDA antiperspirant over-the-counter monograph, zirconium compounds may be added into polymerized aluminum chloride systems to produce aluminum zirconium chlorohydrates, optionally comprising glycine. The zirconium salts are extremely acidic and irritating to the skin. For example, a solution of zirconium oxychloride which is effective as an antiperspirant has a pH of about 0.8. Thus, zirconium oxychloride alone cannot be used in a topical product due to its extremely low pH value.

There is a need for partially neutralized zirconium compounds that overcome the undesirable effects of highly acidic zirconium compounds. In addition, the use of zirconium compounds in oral care formulations has not been reported.

BRIEF SUMMARY

The present invention provides zirconium oxychloride clusters comprising zirconium oxychloride and a basic amino acid e.g., arginine, having a radius of gyration of from 0.5 nm to 50 nm, e.g., from 0.5 nm to 20 nm, from 0.5 nm to 10 nm, from 0.7 nm to 10 nm, from 0.8 nm to 10 nm, from 1 nm to 10 nm, from 0.5 nm to 7 nm, from 0.6 nm to 6 nm, from 0.7 nm to 5 nm, from 0.8 nm to 3 nm, from 0.8 nm to 2.5 nm, or from 1 nm to 2 nm. In some embodiments, the zirconium oxychloride cluster is stable at pH 2-6, 3-5, 3-4, 3.5-4.5, or 4-4.5. In some embodiments, the zirconium oxychloride cluster exhibits a SEC chromatogram having a high peak at 6-8 minutes, 6.5-7.5 minutes, 6.5-7 minutes, or about 6.75 minutes, wherein the SEC chromatogram is obtained under conditions wherein SEC chromatography is carried out using a 10 μm diol-bonded gel filtration column with 20 min run time and 1 mL/min flow rate and the mobile phase of the SEC chromatography consists of deionized water acidified with 1.01% w/w $HNO_3$ to pH 2.3. In some embodiments, the zirconium oxychloride cluster is prepared by a process comprising the steps of: (a) combining a basic amino acid, e.g., arginine, and zirconium oxychloride in an aqueous solution; (b) incubating the solution at a temperature higher than 40° C., e.g., from 40° C. to 60° C., from 45° C. to 55° C., or about 50° C.; and (c) cooling the solution, wherein the molar ratio of the basic amino acid to zirconium oxychloride (basic amino acid/zirconium oxychloride) is less than 1.5, e.g., from 0.5 to 1.5, from 0.7 to 1.3, from 0.8 to 1.2, from 0.9 to 1.1, or about 1. In some embodiments, the zirconium oxychloride cluster may be amorphous.

The present invention also provides oral care products comprising the zirconium oxychloride cluster of the invention. In some embodiments, the oral care product further comprises additional dentin tubule occlusion agents. In some embodiments, the oral care product comprises desensitizing agents.

The present invention also provides methods of preparing the zirconium oxychloride cluster of the invention, comprising the steps of: (a) combining a basic amino acid, e.g., arginine, and zirconium oxychloride in an aqueous solution; (b) incubating the solution at a temperature higher than 40° C., e.g., from 40° C. to 60° C., from 45° C. to 55° C., or about 50° C.; and (c) cooling the solution, wherein the molar ratio of the basic amino acid to zirconium oxychloride in step (a) is less than 1.5, e.g., from 0.5 to 1.5, from 0.7 to 1.3, from 0.8 to 1.2, from 0.9 to 1.1, or about 1.

The present invention also provides use of the zirconium oxychloride cluster of the invention as a dentin tubule occlusion agent.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The present invention will become more fully understood from the detailed description and the accompanying drawings.

DETAILED DESCRIPTION

Figure 1:
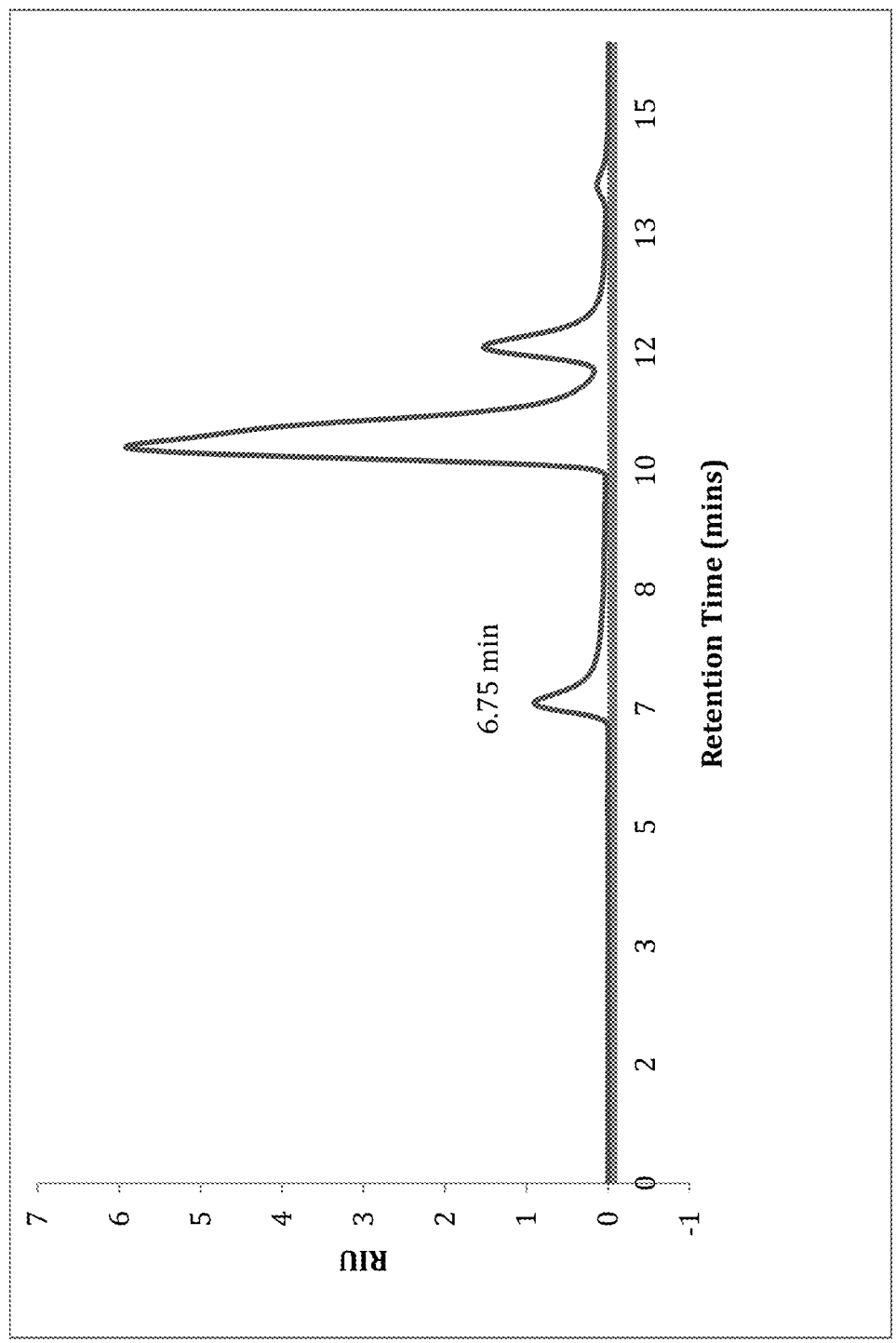
FIG. 1 illustrates a SEC chromatogram of a solution (Arg/Zr 1) in Example 1.

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The present invention provides a zirconium oxychloride cluster (Cluster 1.0) comprising zirconium oxychloride and a basic amino acid e.g., arginine, having a radius of gyration of from 0.5 nm to 50 nm, e.g., from 0.5 nm to 20 nm, from 0.5 nm to 10 nm, from 0.7 nm to 10 nm, from 0.8 nm to 10 nm, from 1 nm to 10 nm, from 0.5 nm to 7 nm, from 0.6 nm to 6 nm, from 0.7 nm to 5 nm, from 0.8 nm to 3 nm, from 0.8 nm to 2.5 nm, or from 1 nm to 2 nm.

1.1. Cluster 1.0, wherein the radius of gyration of the zirconium oxychloride cluster is measured by small angle X-ray scattering (SAXS).
1.2. Cluster 1.0 or 1.1, wherein the zirconium oxychloride cluster is amorphous.
1.3. Any of the preceding clusters, wherein the zirconium oxychloride cluster is stable at pH 2-6, 3-5, 3-4, 3.5-4.5, or 4-4.5.
1.4. Any of the preceding clusters, wherein the zirconium oxychloride cluster exhibits a SEC chromatogram having a high peak at 6-8 minutes, 6.5-7.5 minutes, 6.5-7 minutes, or about 6.75 minutes; and wherein the SEC chromatogram is obtained under conditions wherein SEC chromatography is carried out using a 10 μm diol-bonded gel filtration column with 20 min run time and 1 mL/min flow rate and the mobile phase of the SEC chromatography consists of deionized water acidified with 1.01% w/w $HNO_3$ to pH 2.3.
1.5. Any of the preceding clusters, wherein the basic amino acid is present in an amount of less than 5%, less than 1%, less than 0.1%, less than 0.01%, less than 0.001%, or less than 0.0001%, by weight of the cluster.
1.6. Any of the preceding clusters, wherein the basic amino acid comprises arginine.
1.7. Cluster 1.6, wherein the basic amino acid comprises L-arginine.
1.8. Any of the preceding cluster prepared by a process comprising the steps of:
(a) combining a basic amino acid and zirconium oxychloride in an aqueous solution;
(b) incubating the solution at a temperature higher than 40° C., e.g., from 40° C. to 60° C., from 45° C. to 55° C., or about 50° C.; and
(c) cooling the solution;
wherein the molar ratio of the basic amino acid to zirconium oxychloride in step (a) is less than 1.5.
1.9. Cluster 1.8, wherein the process further comprises the step of purifying the zirconium oxychloride cluster from the cooled solution.
1.10. Cluster 1.9, wherein the zirconium oxychloride cluster is purified by gel permeation chromatography (GPC).
1.11. Cluster 1.10, wherein the GPC column comprises polyacrylamide beads having a wet bead size of less than 45 μm and a 100-1,800 MW fractionation range.
1.12. Cluster 1.11, wherein the purification comprises loading the cooled solution on the GPC column using a HPLC pump at 0.2 mL/min; and the mobile phase of the GPC chromatography is deionized water.
1.13. Cluster 1.12, wherein GPC fraction is collected in the 1160-1300 minute interval and wherein the 1160-1300 minute interval fraction contains the purified zirconium oxychloride cluster.
1.14. Any of Clusters 1.10-1.13, wherein the process further comprises the step of freeze drying the GPC fraction.
1.15. Any of Clusters 1.8-1.14, wherein the molar ratio of the basic amino acid to zirconium oxychloride in step (a) is from 0.5 to 1.5, from 0.7 to 1.3, from 0.8 to 1.2, from 0.9 to 1.1, or about 1.
1.16. Any of Clusters 1.8-1.15, wherein the basic amino acid in step (a) is arginine.
1.17. Cluster 1.16, wherein the basic amino acid in step (a) is L-arginine.
1.18. Any of Clusters 1.8-1.17, wherein the aqueous solution in step (a) is water.

The present invention also provides a method (Method 2.0) for the preparation of a zirconium oxychloride cluster having a radius of gyration of from 0.5 nm to 50 nm, e.g., from 0.5 nm to 20 nm, from 0.5 nm to 10 nm, from 0.7 nm to 10 nm, from 0.8 nm to 10 nm, from 1 nm to 10 nm, from 0.5 nm to 7 nm, from 0.6 nm to 6 nm, from 0.7 nm to 5 nm, from 0.8 nm to 3 nm, from 0.8 nm to 2.5 nm, or from 1 nm to 2 nm, comprising the steps of:
(a) combining a basic amino acid and zirconium oxychloride in an aqueous solution;
(b) incubating the solution at a temperature higher than 40° C., e.g., from 40° C. to 60° C., from 45° C. to 55° C., or about 50° C.; and
(c) cooling the solution;
wherein the molar ratio of the basic amino acid to zirconium oxychloride in step (a) is less than 1.5.
2.1. Method 2.0, wherein the method further comprises the step of purifying the zirconium oxychloride cluster from the cooled solution.
2.2. Method 2.1, wherein the zirconium oxychloride cluster is purified by gel permeation chromatography (GPC).
2.3. Method 2.2, wherein the GPC column comprises polyacrylamide beads having a wet bead size of less than 45 μm and a 100-1,800 MW fractionation range.
2.4. Method 2.3, wherein the purification comprises loading the cooled solution on the GPC column using a HPLC pump at 0.2 mL/min; and the mobile phase of the GPC chromatography is deionized water.
2.5. Method 2.4, wherein GPC fraction is collected in the 1160-1300 minute interval, and wherein the 1160-1300 minute interval fraction contains the purified zirconium oxychloride cluster.
2.6. Any of Methods 2.2-2.5, wherein the method further comprises the step of freeze drying the GPC fraction.
2.7. Any of the preceding methods, wherein the molar ratio of the basic amino acid to zirconium oxychloride in step (a) is from 0.5 to 1.5, from 0.7 to 1.3, from 0.8 to 1.2, or about 1.
2.8. Any of the preceding methods, wherein the basic amino acid in step (a) is arginine.
2.9. Any of the preceding methods, wherein the basic amino acid in step (a) is L-arginine.
2.10. Any of the preceding methods, wherein the aqueous solution in step (a) is water.
2.11. Any of the preceding methods, wherein the radius of gyration of the zirconium oxychloride cluster is measured by small angle X-ray scattering (SAXS).

2.12. Any of the preceding methods, wherein the zirconium oxychloride cluster is amorphous.

2.13. Any of the preceding methods, wherein the zirconium oxychloride cluster is stable at pH 2-6, 3-5, 3-4, 3.5-4.5 or 4-4.5.

2.14. Any of the preceding methods, wherein the zirconium oxychloride cluster exhibits a SEC chromatogram having a high peak at 6-8 minutes, 6.5-7.5 minutes, 6.5-7 minutes, or about 6.75 minutes; and wherein the SEC chromatogram is obtained under conditions wherein SEC chromatography is carried out using a 10 µm diol-bonded gel filtration column with 20 min run time and 1 mL/min flow rate and the mobile phase of the SEC chromatography consists of deionized water acidified with 1.01% w/w $HNO_3$ to pH 2.3.

2.15. Any of the preceding methods, wherein the zirconium oxychloride cluster comprises the basic amino acid.

The term "zirconium oxychloride cluster" herein refers to any zirconium-based cluster comprising zirconium, chloride, oxygen and hydrogen atoms. In some embodiments, the zirconium oxychloride cluster comprises zirconium oxychloride and a basic amino acid. In some embodiments, the zirconium oxychloride cluster may contain a small amount of a basic amino acid. For example, the zirconium oxychloride cluster may contain a basic amino acid in an amount of less than 5%, less than 1%, less than 0.1%, less than 0.01%, less than 0.001%, or less than 0.0001%, by weight of the cluster. The basic amino acid that may be contained in the zirconium oxychloride cluster include, but are not limited to, arginine, lysine, citrullene, ornithine, creatine, histidine, diaminobutanoic acid, diaminopropionic acid, or combinations thereof. In some embodiments, the basic amino acids are selected from arginine, lysine, citrullene, and ornithine. In some embodiments, the basic amino acid comprises arginine, for example, L-arginine.

The zirconium oxychloride cluster of the present invention has a radius of gyration of from 0.5 nm to 50 nm, e.g., from 0.5 nm to 20 nm, from 0.5 nm to 10 nm, from 0.7 nm to 10 nm, from 0.8 nm to 10 nm, from 1 nm to 10 nm, from 0.5 nm to 7 nm, from 0.6 nm to 6 nm, from 0.7 nm to 5 nm, from 0.8 nm to 3 nm, from 0.8 nm to 2.5 nm, or from 1 nm to 2 nm. Radius of gyration (Rg) may be determined by well-known techniques in the art, e.g., small angle X-ray scattering (SAXS) in which X-ray scattering when travelling through the material is measured at small angles. Radius of gyration (Rg) can be calculated from the SAXS data using well-known data processing techniques in the art, e.g., Guinier plot analysis. In some embodiments, radius of gyration (Rg) of the zirconium oxychloride cluster is determined by small angle X-ray scattering (SAXS) using Guinier plot analysis.

In some embodiments, the zirconium oxychloride cluster of the present invention exhibits a SEC chromatogram having a high peak at 6-8 minutes, 6.5-7.5 minutes, 6.5-7 minutes, or about 6.75 minutes, wherein the SEC chromatogram is obtained under conditions wherein SEC chromatography is carried out using a 10 µm diol-bonded gel filtration column, e.g., PAK 125 column by Waters (Milford, MA) with 20 min run time and 1 mL/min flow rate and the mobile phase of the SEC chromatography consists of deionized water acidified with 1.01% w/w $HNO_3$ to pH 2.3.

Size exclusion chromatography (SEC) is a chromatographic method in which molecules in solution are separated by their size, and in some cases molecular weight. SEC provides information on the size of antiperspirant salts in aqueous solutions. For antiperspirant salts including aluminum chlorohydrate, aluminum/zirconium chlorohydrate, and complexes thereof, distinctive peaks have been identified, corresponding to different size populations of the polymer complexes in solution, appearing in a chromatogram as peaks 1, 2, 3, 4 and a peak known as "5,6" (WO2009/075678 and WO2009/076591). Based on the SEC chromatogram, it is predicted that the zirconium oxychloride cluster of the invention has a particle size on the order of nanometer. A peak in this region of retention time is commonly present in various non-activated antiperspirant active salts, but seldom observed in aluminum-free zirconium compounds. In this disclosure, the zirconium oxychloride cluster of the invention exhibiting a SEC chromatogram having a high peak at 6-8 minutes, e.g., about 6.75 minutes is also referred to as "Zr peak 1". The SEC technique is explained fully in WO 2013/158077 and U.S. 2015/0132242, each of which is incorporated by reference herein in its entirety for all purposes.

In some embodiments, the zirconium oxychloride cluster of the present invention is amorphous.

In some embodiments, the zirconium oxychloride cluster of the invention is stable at pH 2-6, 3-5, 3-4, 3.5-4.5 or 4-4.5, in solution, e.g., in aqueous solution. In this disclosure, the zirconium oxychloride cluster is stable means that the cluster does not form a gel or precipitate.

In some embodiments, the zirconium oxychloride cluster may be prepared by a process comprising the steps of: (a) combining a basic amino acid, e.g., arginine, and zirconium oxychloride ($ZrOCl_2.8H_2O$, MW 322.25) in an aqueous solution; (b) incubating the solution at a temperature higher than 40° C. e.g., from 40° C. to 60° C., from 45° C. to 55° C., or about 50° C.; and (c) cooling the solution, wherein the molar ratio of the basic amino acid to zirconium oxychloride is less than 1.5. The solution may be incubated at a temperature higher than 40° C., e.g., from 40° C. to 60° C., from 45° C. to 55° C., or about 50° C. for more than 1 hour, e.g., more than 6 hour, more than 12 hour, more than 1 day, from 1 hour to 2 day, from 6 hour to 2 day, from 12 hour to 2 day, or about 1 day. The term "zirconium oxychloride" herein refers to zirconium oxychloride octahydrate ($ZrOCl_2.8H_2O$, MW 322.25). In the process, low molar ratio of the basic amino acid to zirconium oxychloride in step (a) is critical to obtain stable zirconium oxychloride clusters. When the molar ratio of the basic amino acid to zirconium oxychloride is high, e.g., more than 2, solid gel forms during the process. However, when the molar ratio of the basic amino acid to zirconium oxychloride is low, e.g., less than 1.5, from 0.5 to 1.5, from 0.8 to 1.2, or about 1, the produced zirconium oxychloride clusters are stable in terms of gelation and flocculation. In some embodiments, the molar ratio of the basic amino acid to zirconium oxychloride in step (a) is from 0.5 to 1.5, from 0.7 to 1.3, from 0.8 to 1.2, or about 1. In some embodiments, the aqueous solution in step (a) is water.

In some embodiments, the basic amino acids which can be used in the process of preparing the zirconium oxychloride cluster of the invention include not only naturally occurring basic amino acids, such as arginine, lysine, and histidine, but also any basic amino acids having a carboxyl group and an amino group in the molecule. Accordingly, basic amino acids include, but are not limited to, arginine, lysine, citrullene, ornithine, creatine, histidine, diaminobutanoic acid, diaminopropionic acid, or combinations thereof. In some embodiments, the basic amino acids are selected from arginine, lysine, citrullene, and ornithine. In some embodiments, the basic amino acid is arginine, for example, L-arginine.

In some embodiments, the prepared zirconium oxychloride cluster may be further purified. For example, zirconium oxychloride cluster may be purified by gel permeation chromatography (GPC). Gel permeation chromatography (GPC) is a type of size exclusion chromatography (SEC) that separates molecules on the base of size. In some embodiments, the purification comprises loading the solution containing zirconium oxychloride clusters on the GPC column comprising polyacrylamide beads having a wet bead size of less than 45 μm and a 100-1,800 MW fractionation range, e.g., Bio-Rad P2 gel with 5 μm particle size, using a HPLC pump at 0.2 mL/min; and the mobile phase of the GPC chromatography is deionized water. GPC fraction is collected in the 1160-1300 minute interval and the 1160-1300 minute interval fraction contains the purified zirconium cluster. In some embodiments, the GPC fraction may be freeze dried to obtain purified powder.

Zirconium oxychloride cannot be used in an oral care product due to its extremely low pH value (less than pH 2). However, it has been found that the zirconium oxychloride cluster of the present invention is stable at higher pH. Thus, the zirconium oxychloride cluster can overcome the undesirable effects of highly acidic zirconium compounds. Moreover, it has been found that the zirconium oxychloride cluster of the invention can occlude dentin tubules effectively. Thus, the zirconium oxychloride cluster of the invention can be used as a dentin tubule occlusion agent in oral care products.

The present invention also provides oral care compositions comprising the zirconium oxychloride cluster according to any of Clusters 1.0-1.18. The oral care composition used in the present invention can be in the form of any oral care formulations, including a toothpaste, gel, mouthwash, powder, cream, strip, gum, bead, film, floss or any other known in the art. In some embodiments, the oral care composition used in the present invention is a toothpaste or oral gel. In some embodiments, the oral care composition is a liquid mouthwash, aqueous or non-aqueous gel or paste dentifrice. In some embodiments, the oral care composition is structured mouthwash.

The oral care compositions of the invention contain an orally acceptable carrier. Such materials include but are not limited to, for example, water, humectants, ionic active ingredients, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof. Such materials are well known in the art and are readily chosen by one skilled in the art based on the physical and aesthetic properties desired for the compositions being prepared.

The zirconium oxychloride cluster used in the oral care composition may be prepared by a method according to any of Methods 2.0-2.15. The zirconium oxychloride cluster used in the oral care composition may be a purified or unpurified form.

In some embodiments, the oral care composition of the present invention may further comprise a basic amino acid, e.g., arginine, in addition to the basic amino acid present in zirconium oxychloride clusters. The basic amino acids which can be used in the compositions include not only naturally occurring basic amino acids, such as arginine, lysine, and histidine, but also any basic amino acids having a carboxyl group and an amino group in the molecule, which are water-soluble and provide an aqueous solution with a pH of about 7 or greater. Accordingly, basic amino acids include, but are not limited to, arginine, lysine, citrullene, ornithine, creatine, histidine, diaminobutanoic acid, diaminopropionic acid, salts thereof or combinations thereof. In a particular embodiment, the basic amino acids are selected from arginine, lysine, citrullene, and ornithine. In some embodiments, the basic amino acid is arginine, for example, L-arginine, or a salt thereof.

The oral care composition of the present invention may further comprise dentin tubule occlusion agents other than the zirconium oxychloride cluster of the present invention. Such dentin tubule occlusion agents include, but are not limited to, arginine-calcium carbonate complexes, silicas, polymethyl vinyl ether-maleic acid (PMV/MA) copolymers, oxalate salts, strontium salts, and combinations thereof.

The oral care composition of the present invention may include desensitizing agents. Such desensitizing agents include, but are not limited to, potassium salts such as potassium nitrate, potassium bicarbonate, potassium chloride, potassium citrate, potassium tartrate, and potassium oxalate, capsaicin, eugenol, strontium salts, zinc salts, chloride salts, and combinations thereof. Such agents may be added in effective amounts, which preferably vary between about 0.01% to about 10% by weight based on the total weight of the composition, depending on the agent chosen. In some embodiments, the desensitizing agent is a potassium salt in an amount of at least about 5% by weight of a potassium salt based on the total weight of the composition, e.g., from about 5?/k to about 10% by weight of a potassium salt based on the total weight of the composition. In some embodiments, the desensitizing agent is potassium nitrate.

The oral care composition of the present invention may include one or more fluoride ion sources, e.g., soluble fluoride salts. A wide variety of fluoride ion-yielding materials can be employed as sources of soluble fluoride in the present compositions. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments, the fluoride ion source includes stannous fluoride, sodium fluoride, sodium monofluorophosphate as well as mixtures thereof. In certain embodiments, the oral care composition described herein may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions described herein at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counter ion in the salt.

The oral care compositions of the present invention may include other active ingredients. The active ingredients include, for example, zinc ion sources, anti-bacterial active agents, anti-tartar agents, anti-caries agents, anti-inflammatory agents, anti-sensitivity agents, basic amino acids, e.g., arginine, enzymes, nutrients, and the like. Actives useful herein are optionally present in the compositions of the present invention in safe and effective amounts that are sufficient to have the desired therapeutic or prophylactic effect in the human or lower animal subject to whom the active is administered, without undue adverse side effects (such as toxicity, irritation, or allergic response), commensurate with a reasonable risk/benefit ratio when used in the manner of this invention. The specific safe and effective amount of the active will vary with such factors as the particular condition being treated, the physical condition of the subject, the nature of concurrent therapy (if any), the specific active used, the specific dosage form, the carrier employed, and the desired dosage regimen.

One or more abrasive or polishing materials may also be included in the oral care compositions of the present invention. The abrasive or polishing material can be any material that is acceptable for use in a dentifrice, does not excessively abrade dentin and is compatible with the other components of the oral care composition. Exemplary abrasive or polishing materials include, but are not limited to: silica abrasives, calcium phosphate abrasives, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, and combinations thereof.

The oral care composition of the present invention may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the composition. Polyoxyethylene is also commonly known as polyethylene glycol ("PEG") or polyethylene oxide. The polyoxyethylenes suitable for this composition will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions. Where present, the amount of foaming agent in the oral care composition (i.e., a single dose) is about 0.01 to about 0.9% by weight, about 0.05 to about 0.5% by weight, and in another embodiment about 0.1 to about 0.2% by weight.

The oral care compositions of the present invention may include at least one surfactant or solubilizer. Suitable surfactants include neutral surfactants (such as polyoxyethylene hydrogenated castor oil or fatty acids of sugars), anionic surfactants (such as sodium lauryl sulfate), cationic surfactants (such as the ammonium cation surfactants) or zwitterionic surfactants. These surfactants or solubilizers may be present in amounts of typically 0.01% to 2%; or from 1% to 2%; or about 1.5%, by weight of the composition.

The oral care compositions of the present invention may include one or more humectants. Humectants can reduce evaporation and also contribute towards preservation by lowering water activity, and can also impart desirable sweetness or flavor to compositions. Suitable humectants include edible polyhydric alcohols such as glycerin, sorbitol, xylitol, propylene glycol as well as other polyols and mixtures of these humectants. Other useful materials may also include orally acceptable alcohols, or polymers, e.g., such as polyvinylmethyl ether maleic acid copolymers, polysaccharides (e.g. cellulose derivatives, for example carboxymethyl cellulose, or polysaccharide gums, for example xanthan gum or carrageenan gum). In some embodiments, the humectant can be present in an amount of from 20% to 60%, for example from 30% to 50%, for example from 40% to 45%, by weight of the composition.

The oral care compositions of the present invention may include a preservative. Suitable preservatives include, but are not limited to, sodium benzoate, potassium sorbate, methylisothiazolinone, paraben preservatives, for example methyl p-hydroxybenzoate, propyl p-hydroxybenzoate, and mixtures thereof.

The oral care compositions of the present invention may include a sweetener such as, for example, saccharin, for example sodium saccharin, acesulfam, neotame, cyclamate or sucralose; natural high-intensity sweeteners such as thaumatin, stevioside or glycyrrhizin; or such as sorbitol, xylitol, maltitol or mannitol. One or more of such sweeteners may be present in an amount of from 0.005% to 5% by weight, for example 0.01% to 1%, for example 0.01% to 0.5%, by weight of the composition.

The oral care compositions of the present invention may include a flavoring agent. Suitable flavoring agents include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. The flavoring agent is typically incorporated in the oral composition at a concentration of 0.01 to 3% by weight.

The present invention provides methods for treating, preventing or ameliorating a symptom associated with dentin hypersensitivity, comprising administering the zirconium oxychloride cluster as described herein.

The present invention also provides use of the zirconium oxychloride cluster as described herein as a dentin tubule occlusion agent.

EXAMPLES

Example 1: Preparation of Zirconium Oxychloride Clusters

Samples were prepared according to Table 1. Water was added to zirconium oxychloride ($ZrOCl_2.8H_2O$, MW 322.25) in a glass jar to yield a clear solution containing 1% zirconium oxychloride. Under stirring, L-arginine was slowly added to prevent clumping of arginine as well as large fluctuations in localized pH values. The molar ratio of arginine to zirconium oxychloride was 0.5:1, 1:1, 2:1, 3:1, and 4:1, as shown in Table 1. The solutions were incubated for 1 day at 50° C. Then the solutions were cooled to room temperature. Solid gel was formed in samples with the molar ratio of arginine to zirconium oxychloride of 2-4. However, at the molar ratio of arginine to zirconium oxychloride to 0, 0.5 and 1, the samples were stable in terms of gelation and flocculation with pH of 1.39, 1.73, and 2.59, respectively.

TABLE 1

1% zirconium oxychloride with varied arginine

| | Calculated | | | | Experimental | | | | |
|---|---|---|---|---|---|---|---|---|---|
| Sample | Arg/Zr mol | Zr g | Arg g | Total g | Arg/Zr mol | Zr g | Arg g | Total g | pH |
| Zr | 0 | 0.3533 | 0 | 10 | 0 | 0.3533 | 0 | 9.9928 | 1.39 clear |
| Arg/Zr 0.5 | 0.5 | 0.3533 | 0.0955 | 10 | 0.49 | 0.3531 | 0.0944 | 9.9955 | 1.73 clear |
| Arg/Zr 1 | 1 | 0.3533 | 0.1910 | 10 | 1.00 | 0.3534 | 0.1912 | 10.0117 | 2.59 clear |
| Arg/Zr 2 | 2 | 0.3533 | 0.3819 | 10 | 2.00 | 0.3540 | 0.3818 | 10.0140 | gel |
| Arg/Zr 3 | 3 | 0.3533 | 0.5729 | 10 | 2.99 | 0.3541 | 0.5729 | 9.9993 | gel |
| Arg/Zr 4 | 4 | 0.3533 | 0.7638 | 10 | 4.01 | 0.3526 | 0.7639 | 9.9970 | gel |

SEC-RI analysis was carried out on the sample with Arg/Zr molar ratio of 1. SEC was equipped with a differential refractive index (dRI) detector. Separation was carried out using a Protein Pak 125 column by Waters (Milford, MA) with 20 min run time and 1 mL/min flow rate. The mobile phase consisted of deionized water acidified with 1.01% w/w $HNO_3$ to pH 2.3. SEC chromatogram exhibited a peak at 6.75 minute (FIG. 1). A peak in this region of retention time is commonly present in various non-activated antiperspirant active salts, but seldom observed in aluminum-free zirconium compounds. Based on the SEC data, it was predicted that the prepared zirconium compound is a zirconium-based cluster (zirconium oxychloride cluster) with a particle size of the order of nanometer. Synchrotron-small-angle X-ray scattering (SAXS) analysis was further carried out to determine the radius of gyration of the zirconium oxychloride cluster. The distribution of radius of gyration was extracted from the SAXS data using Guinier plot analysis. There existed a main peak near 1.1 nm and a small shoulder peak near 2 nm. The SAXS analysis showed that radius of gyration of most zirconium oxychloride clusters is within 0.8 nm-3 nm.

Example 2: Purification of Zirconium Oxychloride Clusters

A 100 g batch was prepared according to Table 2. 1% w/w zirconium oxychloride ($ZrOCl_2 \cdot 8H_2O$, MW 322.25) and arginine were mixed in aqueous solution with the molar ratio of arginine to zirconium oxychloride of 1:1.

TABLE 2

1% zirconium oxy chloride with arginine (1:1 ratio) (100 g batch)

| | Calculated | | | | Experimental | | | | |
|---|---|---|---|---|---|---|---|---|---|
| Sample | Arg/Zr mol | Zr g | Arg g | Total g | Arg/Zr mol | Zr g | Arg g | Total g | pH |
| Arg/Zr 1 | 1 | 3.5325 | 1.9096 | 100 | 1 | 3.53 | 1.91 | 100.06 | 2.31 |

Figure 2:
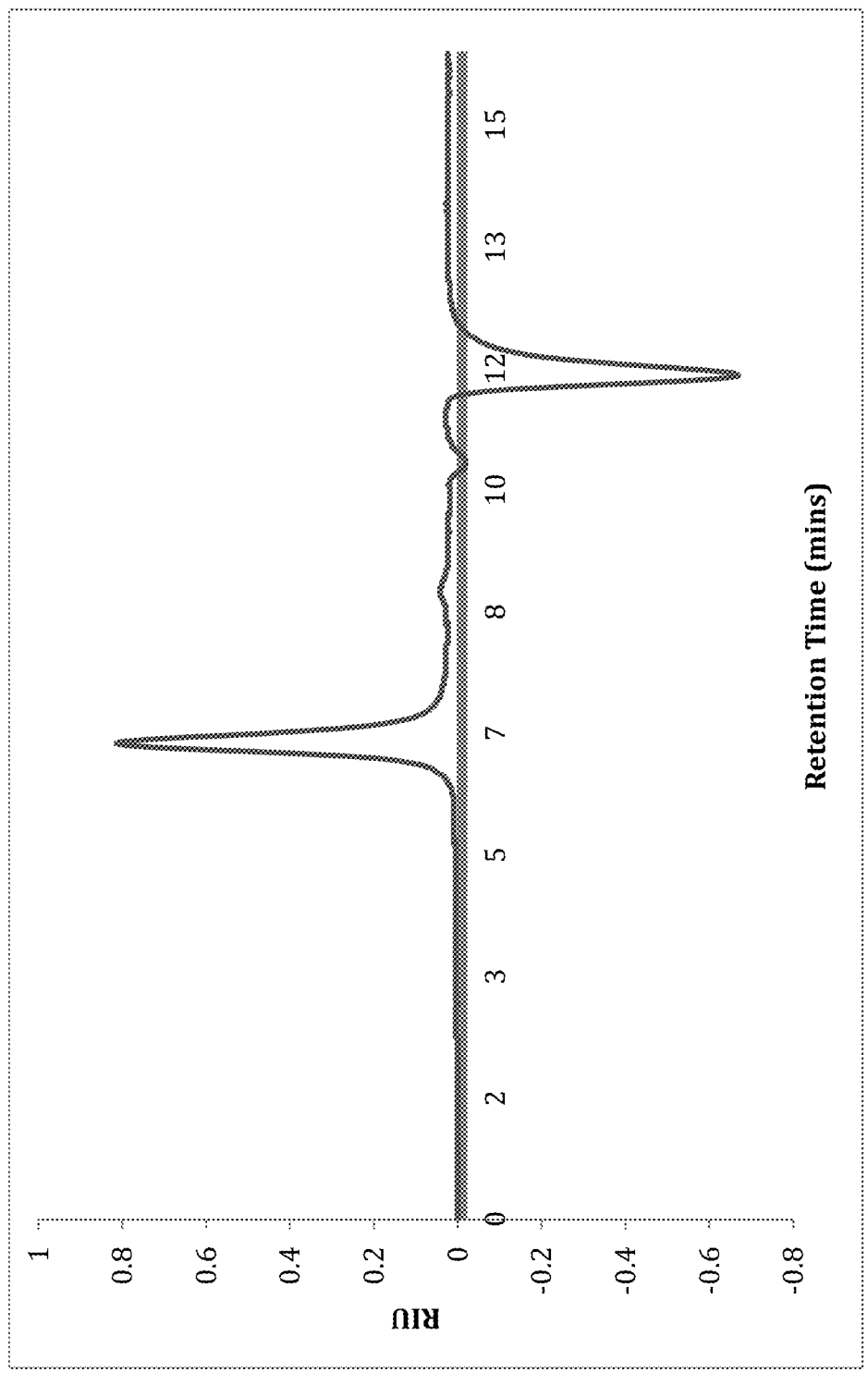
FIG. 2 illustrates a SEC chromatogram of the GPC fraction 1160-1300 min in Example 2.

The zirconium oxychloride cluster was prepared as described in Example 1. The prepared zirconium oxychloride cluster was purified by gel permeability chromatograph (GPC). GPC column was prepared using Bio-Rad P2 gel with 5 μm particle size. Approximately 10 mL of prepared solution was filtered (0.45 μm) and loaded on the column using a HPLC pump at 0.2 mL/min. The mobile phase of the GPC chromatography was deionized water. Elution fractions were collected in intervals and monitored using SEC-RI. The first species to elute exhibited a peak of SEC at 6.75 minute indicative of the zirconium oxychloride clusters. Highest concentration of the zirconium oxychloride clusters was observed in the 1160-1300 min GPC fraction. SEC-RI chromatogram of GPC fraction 1160-1300 min is shown in FIG. 2. The pH of the GPC fraction (1160-1300 min) was 4.5. The zirconium oxychloride cluster in this GPC fraction was stable in terms of gelation and flocculation. 10 g of this fraction was freeze dried to obtain purified powder for subsequent PXRD analysis. PXRD (Powder X-Ray Diffraction) analysis revealed non-crystalline packing arrangements, indicating the zirconium oxychloride cluster is amorphous.

Example 3. Occlusion of Dentin Tubules

Human teeth were mounted on a Buehler Saw (Lake Bluff, IL) and cross-sectioned in slices of 800 μm thickness. Dentin sections were then sanded and polished on the Buehler EcoMet III polish grinder with a Buehler polishing cloth (Lake Bluff, IL) and a 5 μm alumina slurry. Sections were sonicated in deionized water, etched in 1% citric acid solution and sonicated again in deionized water to ensure tubules were open and clean. Baseline confocal images were then taken. Zirconium oxychloride cluster was prepared as described in Example 1. Specifically, 94.6 g of water was added to 3.5377 g of zirconium oxychloride ($ZrOCl_2 \cdot 8H_2O$) in a glass jar to yield a clear solution. Under stirring, 1.9104 g of L-arginine was slowly added to prevent clumping of arginine as well as large fluctuations in localized pH values. This clear solution was heated at 50° C. for 24 hours. Then the solution was cooled to room temperature. A drop of the zirconium oxychloride cluster solution was placed on the dry dentin surface and allowed to sit at room temperature for 15 minutes. Each section was then stirred in 20 mL of PBS at 130 rpm for 15 minutes at room temperature. Jars were gently shaken back and forth three times before the samples were removed and dried. This procedure was repeated 5 times. Confocal images were taken after the five treatments. Validation of occlusion performance was analyzed with confocal microscopy (Leica DCM 3D—reflectance at 150×). Mean percent occlusion was calculated on two dentin samples, and 10 data points were analyzed for each sample.

The total area occupied by the grains (or open tubules) before and after treatment was measured and % occlusion was calculated as follows:

% Occlusion=100−($R2/R1$×100)

where R1 represents the total area occupied by the open dentin tubules for the untreated dentin, and R2 represents total area occupied by the open dentin tubules for treated dentin.

Figure 3:
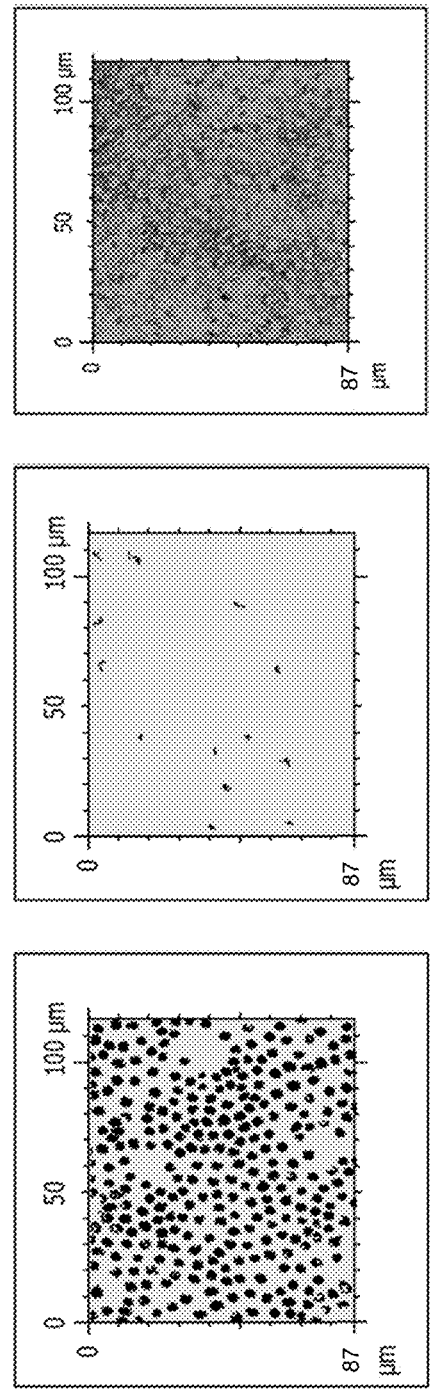
FIG. 3 illustrates an image of dentin sections before and after treatment with the zirconium oxychloride cluster.
Figure 3:
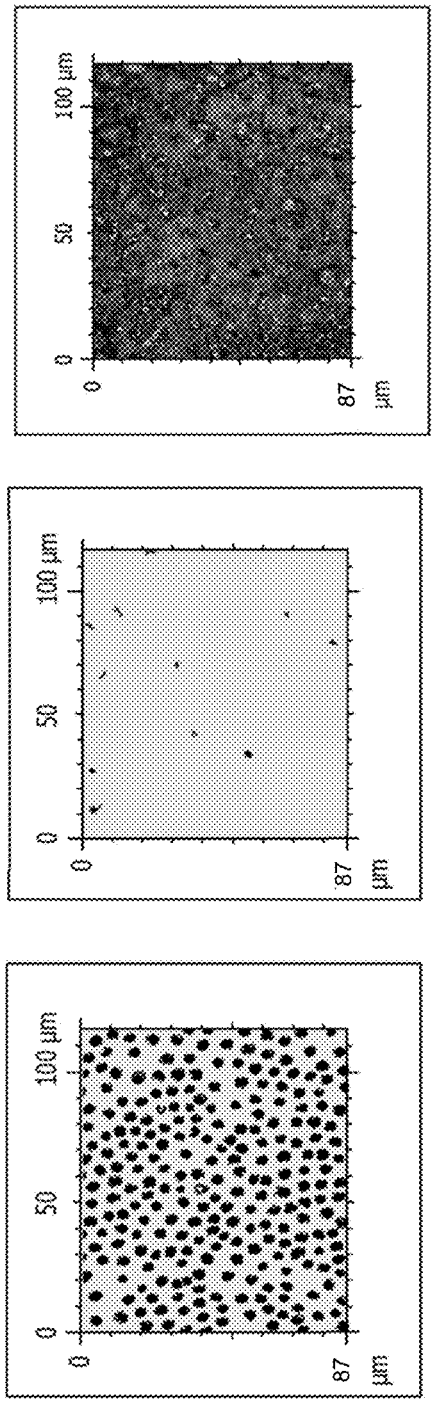

The results are presented in Tables 3 and 4. Images of dentin sections before and after treatment are shown in FIG. 3.

TABLE 3

Calculated areas of open dentin tubules before and after treatment

| Data point | Before Treatment ($\mu m^2$) | After Treatment ($\mu m^2$) | Percent Occlusion ($\mu m^2$) |
|---|---|---|---|
| Sample 1 | | | |
| 1a | 1921.88 | 326.09 | 83.03 |
| 1b | 2787.55 | 36.23 | 98.70 |
| 1c | 2788.07 | 34.00 | 98.78 |
| 1d | 1927.76 | 41.61 | 97.84 |
| 1e | 1576.52 | 0.00 | 100.00 |
| 1f | 690.83 | 0.00 | 100.00 |
| 1g | 3275.50 | 0.00 | 100.00 |
| 1h | 3407.34 | 29.11 | 99.15 |
| 1i | 4103.59 | 0.00 | 100.00 |
| 1j | 3609.39 | 8.84 | 99.76 |
| Sample 2 | | | |
| 2a | 2191.99 | 0.00 | 100.00 |
| 2b | 2922.52 | 55.90 | 98.09 |
| 2c | 2306.50 | 198.08 | 91.41 |
| 2d | 1608.31 | 203.07 | 97.37 |
| 2e | 1842.89 | 18.85 | 98.98 |
| 2f | 2831.15 | 0.00 | 100.00 |
| 2g | 2808.12 | 0.00 | 100.00 |
| 2h | 1972.22 | 26.71 | 98.65 |
| 2i | 1318.12 | 30.54 | 97.68 |
| 2j | 2811.60 | 0.00 | 100.00 |

TABLE 4

Average percent occlusion after treatment

| | Occlusion (%) |
|---|---|
| Dentin Sample 1 | 97.73 ± 1.65 |
| Dentin Sample 2 | 97.22 ± 1.36 |

The in-vitro confocal microscopy results on human teeth show that the zirconium oxychloride cluster provides significant (>97%) dentin tubule occlusion. These results suggest that the zirconium oxychloride cluster can be used as a dentin tubule occlusion agent.

While the disclosure has been described with respect to specific examples including presently preferred modes of carrying out the disclosure, those skilled in the art will appreciate that there are numerous variations and permutations of the above described systems and techniques. It is to be understood that other embodiments may be utilized and structural and functional modifications may be made without departing from the scope of the present disclosure. Thus, the scope of the disclosure should be construed broadly as set forth in the appended claims.

The invention claimed is:

1. An oral care composition comprising a zirconium oxychloride cluster consisting of:
    a. zirconium oxychloride; and
    b. a basic amino acid;
wherein the cluster has a radius of gyration of from 0.5 nm to 50 nm, wherein the cluster occludes dentin tubules effectively, and wherein the composition is selected from a dentifrice, toothpaste, tooth powder, or mouthwash.

2. The oral care composition of claim 1, further comprising a dentin tubule occlusion agent other than the zirconium oxychloride cluster.

3. The oral care composition of claim 1, further comprising a desensitizing agent selected from potassium nitrate, potassium bicarbonate, potassium chloride, potassium citrate, potassium tartrate, potassium oxalate, capsaicin, eugenol, a strontium salt, a zinc salt, a chloride salt, and a combination of two or more thereof.

4. The oral care composition of claim 1, further comprising a fluoride ion source.

5. The composition of claim 1, wherein the basic amino acid comprises arginine.

6. The composition of claim 1, wherein the zirconium oxychloride cluster is stable at pH 2-6, 3-5, 3-4, 3.5-4.5 or 4-4.5.

7. A method for treating, preventing or ameliorating a symptom associated with dentin hypersensitivity, comprising administering a composition according to claim 1, to a subject in need thereof.

* * * * *